United States Patent [19]

Johnson et al.

[11] Patent Number: 4,980,366

[45] Date of Patent: Dec. 25, 1990

[54] AMIDE, SULFONAMIDE, UREA, CARBAMATE, THIOCARBAMATE, AND THIOUREA DERIVATIVES OF 4'HYDROXYBENZYLAMI HAVING ANTI-INFLAMMATORY AND ANALGESIC ACTIVITY

[75] Inventors: Graham Johnson, Ann Arbor, Mich.; Michael F. Rafferty, N. Bradford, Conn.

[73] Assignee: Warner-Lambert Co., Morris Plains, N.J.

[21] Appl. No.: 324,966

[22] Filed: Mar. 16, 1989

Related U.S. Application Data

[63] Continuation of Ser. No. 898,160, Aug. 19, 1986, abandoned.

[51] Int. Cl.$^5$ .................... A61K 31/18; A61K 7/155; A61K 31/165; C07C 103/00; C07C 103/063; C07C 153/063
[52] U.S. Cl. ..................... 514/381; 514/396; 514/588; 514/596; 514/597; 514/598; 514/601; 514/602; 514/603; 514/604; 514/605; 514/625; 514/626; 514/627; 514/628; 514/629; 514/630; 260/404; 548/252; 548/253; 548/352; 548/355; 560/23; 564/56; 564/99; 564/218; 564/219; 564/220; 564/221; 564/223
[58] Field of Search ............ 260/404; 560/23; 514/625–630, 601–605, 588, 596–598, 381, 396; 564/56, 99, 218–223; 548/352, 355, 252, 253

[56] References Cited

U.S. PATENT DOCUMENTS

| | | |
|---|---|---|
| 2,652,428 | 9/1953 | Weissberger et al. ............... 564/99 |
| 3,004,035 | 10/1961 | Csendes ............................ 564/56 X |
| 3,008,969 | 11/1961 | Pretra ............................... 560/29 X |
| 3,057,868 | 10/1962 | Ishidate et al. .................. 564/219 X |
| 3,621,043 | 11/1971 | Seki et al. ......................... 260/404 |
| 3,741,999 | 6/1973 | Seki et al. ......................... 260/404 |
| 3,780,103 | 12/1973 | Knell ............................... 564/219 X |
| 4,179,499 | 12/1979 | Christensen .................... 514/627 X |
| 4,313,958 | 2/1982 | Lahann ............................. 514/627 |
| 4,401,663 | 8/1983 | Buckwalter et al. ............. 564/99 X |
| 4,493,848 | 1/1985 | Lahann et al. .................... 514/627 |
| 4,522,759 | 6/1985 | Yamatsu et al. .................. 260/404 |
| 4,532,139 | 7/1985 | Janusz et al. ..................... 514/627 |
| 4,544,669 | 10/1985 | Lahann et al. ................. 260/404 X |
| 4,564,476 | 1/1986 | Ho .................................. 514/627 X |
| 4,599,342 | 7/1986 | Lahann ............................. 514/627 |
| 4,689,182 | 8/1987 | Rafferty et al. .................... 260/404 |

FOREIGN PATENT DOCUMENTS

| | | | |
|---|---|---|---|
| 0132113 | 1/1985 | European Pat. Off. ............ 260/404 |
| 2106816 | 8/1971 | Fed. Rep. of Germany ...... 260/404 |
| 59-216864 | 12/1984 | Japan ................................. 560/29 |
| 2144416 | 3/1985 | United Kingdom ................ 514/627 |

OTHER PUBLICATIONS

Hayes et al., Chemical Abstracts, vol. 100, No. 203126b (1984).

Johnson et al., Chemical Abstracts, vol. 100, No. 79837t (1984).

Jones et al., J. Chem. Soc. (London), vol. 127, pp. 2588 to 2598, (1925).

Nelson et al., J. Amer. Chem. Soc., vol. 45, pp. 2179 to 2181 (1923).

Sciortino et al., Chemical Abstracts, vol. 70, No. 37347q (1969).

Sekiya et al., Chemical Abstracts, vol. 67, No. 11359h (1967).

Smith et al., Chemical Abstracts, vol. 75, No. 140481f (1971).

Primary Examiner—Floyd D. Higel
Attorney, Agent, or Firm—Joan Thierstein

[57] ABSTRACT

Novel 4'-hydroxybenylamine derivatives of the formula

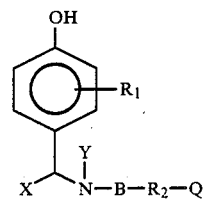

pharmaceutical compositions and methods of use thereof are the present invention. Utility is for the treatment of arthritis, asthma, Raynaud's disease, inflammatory bowel disorders, trigeminal or herpetic neuralgia, inflammatory eye disorders, psoriasis, dental pain, and headaches, particularly vascular headache, succh as migraine, cluster, mixed vascular syndromes, as well as nonvascular, tension headaches.

15 Claims, No Drawings

AMIDE, SULFONAMIDE, UREA, CARBAMATE, THIOCARBAMATE, AND THIOUREA DERIVATIVES OF 4'HYDROXYBENZYLAMI HAVING ANTI-INFLAMMATORY AND ANALGESIC ACTIVITY

This application is a continuation of U.S. application Ser. No. 06/898,160, filed Aug. 19, 1986, now abandoned.

BACKGROUND OF THE PRESENT INVENTION

The present invention is novel compounds, which are derivatives of hydroxybenzylamine and as such are related to capsaicin. The present compounds have anti-inflammatory activity for the treatment of arthritis, asthma, Raynaud's disease, inflammatory bowel disorders, trigeminal or herpetic neuralgia, inflammatory eye disorders, psoriasis, and/or having analgesic activity for the treatment of dental pain and headache, particularly vascular headache, such as migraine, cluster, and mixed vascular syndromes, as well as nonvascular, tension headache. Thus, the present invention is also a pharmaceutical composition comprising the novel compounds together with a pharmaceutically acceptable carrier or methods of use of such compounds for treatment of the above noted conditions.

Among known compounds are benzoic acid derivations in which the derivative is limited to a substituent having a (naphthoxy)isobutyramido containing group and for which compounds an antiphlogistic activity is disclosed. See U.S. Pat. No. 4,183,954. Additionally O. Exner, et al. discloses N-(4-carboxybenzyl)acetamide in "Quantitative Evaluation of the Inductive Effect," Coll. Czech. Chem. Commun. 27, 2299 (1962). But no teaching to activity or utility for the compound is indicated by Exner, et al.

Selected compounds related to capsaicin are disclosed in a series of patents. Such disclosed compounds have various amido, sulfonylamido or amidosulfonyl and thioamido linkages in combination with a benzyl or a benzyl analog moiety and may be found in U.S. Pat. Nos. 4,443,473, having a parahydroxybenzyl; 4,313,958, that has a paramethoxybenzyl and claims the use of capsaicin; U.S. Pat. Nos. 4,460,602 having a para-hydroxybenzyl; 4,401,663 having a para-hydroxy- or methoxybenzyl; European Patent Application No. 0,132,113 having a para-hydroxybenzyl; U.S. Pat. No. 4,424,203 having a para-hydroxy- or, alkyloxybenzyl; European Patent Application No. 0,132,114 having a para-hydroxy or alkoxybenzyl; European Patent Application No. 0,132,346 having a para-hydroxy or alkyloxy-benzyl and European Patent Application No. 0,132,115 having a para-hydroxybenzyl; as well as European Patent Application Nos. 0,149,544 and 0,149,545 both of which may have a para-hydroxybenzyl moiety. Of these European Patent Applications Nos. 0,132,115; 0,132,346; 0,132,113; 0,132,114; 0,132,115, 0,149,544 and 0,149,545 include a short chain acyl group on the benzyl moiety. Analgesia is disclosed as an activity for the compounds of the references. However, none of the references teach the compounds having the combination of moieties of the present invention.

Additionally, related benzoic acid and benzoic acid ester derivatives having antiinflammatory and analgesic activity are found in co-pending U.S. application Ser. No. 811,567 filed Dec. 20, 1985, and now U.S. Pat. No. 4,869,182, which refers to most of the above noted references. Therefore, U.S.S.N. No. 811,567 is hereby incorporated by reference.

DETAILED DESCRIPTION OF INVENTION

The novel compounds of the present invention have the following structural formula:

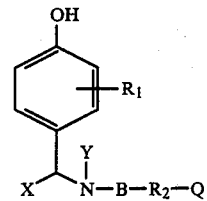

and pharmaceutically acceptable acid addition or base salts thereof; wherein:

(a) $R_1$ is (i) R wherein R is lower alkyl or NR'R" wherein R' and R" are independently hydrogen or lower alkyl, (ii) halogen, (iii) trifluoromethyl, (iv) $NO_2$, (v) $SCH_3$, (vi) $SO_2R'$ wherein R' is as defined above, (vii) $CO_2R'$ wherein R' is as defined above, (viii) NHCOR' wherein R' is as defined above, (ix) CN, or (X) 5-tetrazolyl;

(b) B is

 (B₁)

 (B₂)

 (B₃)

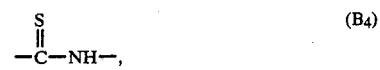 (B₄)

 (B₅)

 (B₆)

(c) X and Y are independently H or lower alkyl;
(d) $R_2$ is alkylenyl, alkenylenyl, alkynylenyl of 1 to 23 carbons, inclusive;
(e) Q is (i) $R_3$ wherein $R_3$ is lower alkyl or NR'R" wherein R' and R" are independently as defined above; (ii) halogen; (iii) trifluoromethyl; (iv) $NO_2$; (v) $SCH_3$; (vi) $SO_2R'$ wherein R' is independently as defined above; (vii) COR' wherein R' is independently as defined above; (viii) NHCOR' wherein R' is independently as defined above; (ix) CN; (x) tetrazolyl; (xi) imidazolyl; (xii) cyclohexyl; (xiii) phenyl; or

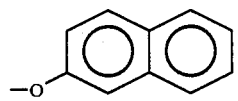 (xiv)

The term "lower alkyl" means a hydrocarbon chain up to 4 carbon atoms such as methyl, ethyl, propyl, or butyl, and isomers thereof.

The terms alkylenyl, alkenylenyl, and alkynylenyl are divalent hydrocarbon straight or branched chains containing one or more single, double or triple carbon to carbon bonds, respectively.

Preferred embodiments of the present invention contain the $R_1$ substituent as shown in the following formula (II):

Preferred embodiments of the present invention contain the $R_1$ substituent as shown in the following formula (II):

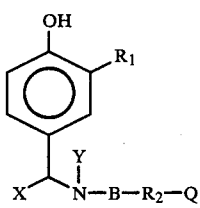

II wherein X, Y, B, $R_2$ and Q are all as defined above. More preferred embodiments of the present invention are compounds of formula II wherein B is $B_1$ and X, Y, $R_2$ and Q are as defined above. The most preferred embodiments of the present invention is the compound N-[(3-chloro-4-hydroxyphenyl)methyl]nonamide, N-[(4-hydroxy-3-methylphenyl)methyl]nonamide, or N-[[4-hydroxy-3-(methylthio)phenyl]methyl]nonamide.

The preferred method of use is for treating headaches, particularly migraine headaches.

Examples of suitable acids for the preparation of the acid addition salts are inorganic acids such as hydrochloric acid, hydrobromic acid, sulfuric acid, phosphoric acid, and the like, and organic acids such as acetic acid, benzoic acid, tartaric acid, fumaric acid, succinic acid, maleic acid, arginine acid, lactic acid, tartaric acid, and sulfonic acids such as methansulfonic acid, ethansulfonic acid, benzenesulfonic acid or p-toluenesulfonic acid.

The base salts of the present inventions include those safe for topical or systemic administration, such as sodium, potassium, calcium, magnesium, and ammonium salts or the like.

Generally, the preparation of the compounds of the present invention is represented by the following scheme:

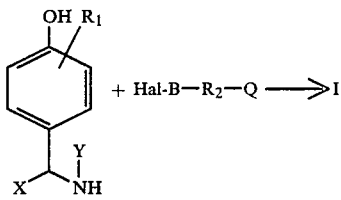

wherein $R_1$, X, Y, B, $R_2$, Q are as defined above and Hal is chloro, bromo, but preferably chloro.

The preparation uses standard synthetic techniques used in the examples or analogous to those used in the examples hereinafter. The starting materials for the preparation are readily available, known or can be prepared by known methods.

More specifically, preparation of the compounds of formula I wherein B is $B_1$ are analogous to those well known in the art using variations in conditions and having starting materials known or readily prepared within the skill of an ordinary artisan.

The compounds of formula I wherein B is $B_2$, $B_3$, $B_4$, $B_5$ or $B_6$ are likewise prepared by methods analogous to those well known in the art using variations in conditions and having starting materials known or readily prepared by an artisan. Such methods are shown as follows in Schemes I through V respectively as follows:

Scheme I

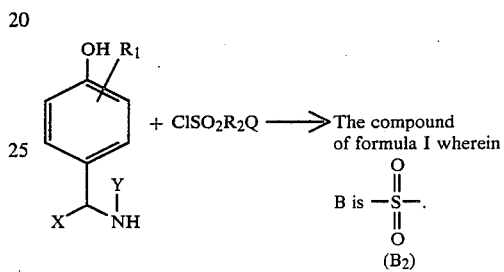

Scheme II

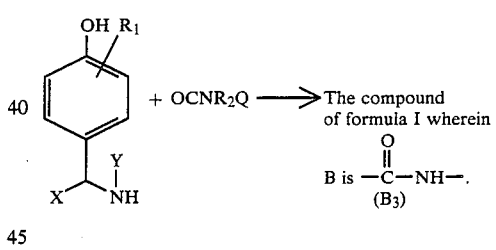

Scheme III

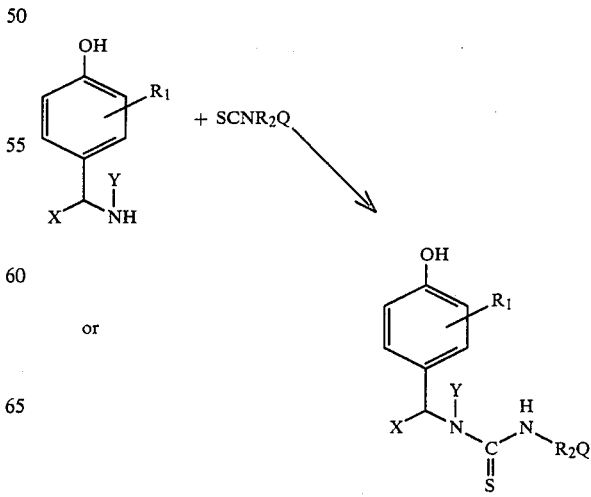

-continued
Scheme III

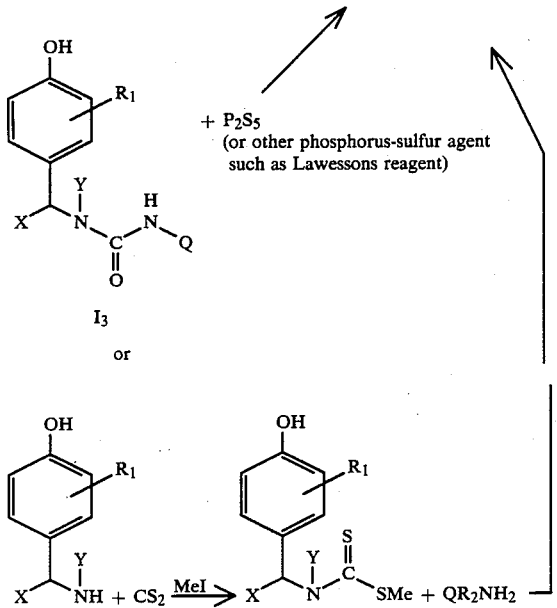

Scheme IV

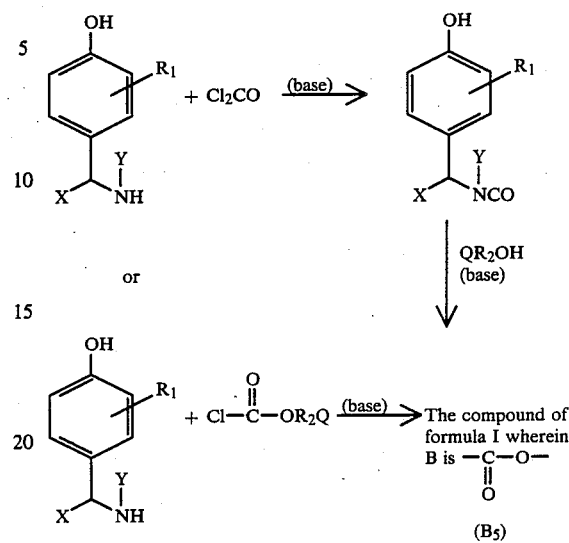

Scheme V

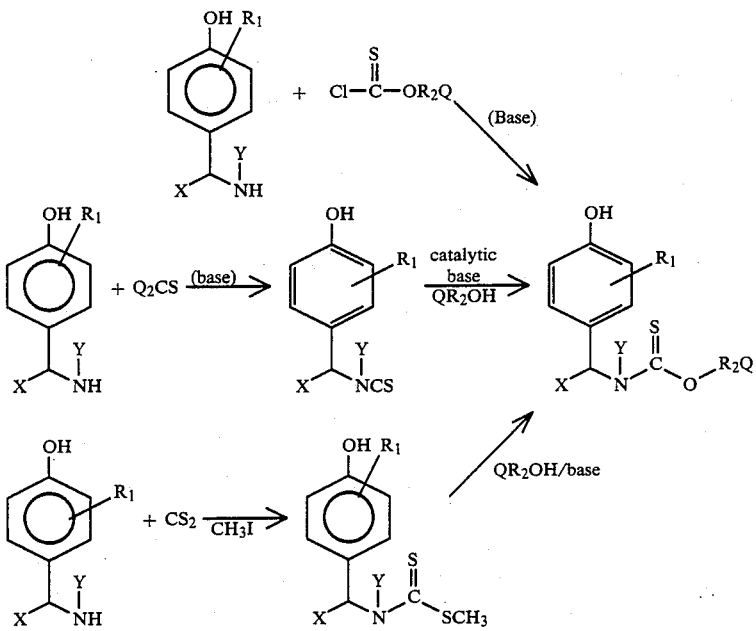

Under certain circumstances it is necessary to protect either the N or O of intermediates in the above noted processes, with suitable protecting groups which are known. Introduction and removal of such suitable oxygen and nitrogen protecting groups are well-known in the art of organic chemistry; see for example "Protective Groups in Organic Chemistry," J. F. W. McOmie, ed., (New York, 1973), pages 43ff, 95ff, J. F. W. McOmie, *Advances in Organic Chemistry*, Vol. 3, 191–281 (1963); R. A. Borssonas, *Advances in Organic Chemistry*, Vol. 3, 159–190 (1963); and J. F. W. McOmie, *Chem. & Ind.*, 603 (1979).

Examples of suitable oxygen protecting groups are benzyl, t-butyldimethylsilyl, ethoxyethyl, and the like. Protection of an N-H containing moiety is necessary for some of the processes described herein for the preparation of compounds of this invention. Suitable nitrogen protecting groups are benzyl, triphenylmethyl, trialkylsilyl, trichloroethylcarbamate, trichloroethoxycarbonyl, vinyloxycarbamate, and the like.

Under certain circumstances it is necessary to protect two different oxygens with dissimilar protecting groups such that one can be selectively removed while leaving the other in place. The benzyl and t-butyldimethylsilyl groups are used in this way; either is removable in the presence of the other, benzyl being removed by catalytic hydrogenolysis, and t-butyldimethylsilyl being removed by reaction with, for example, tetra-n-butylammonium fluoride.

In the process described herein for the preparation of compounds of this invention the requirements for protective groups are generally well recognized by one skilled in the art of organic chemistry, and accordingly the use of appropriate protecting is necessarily implied by the processes of the charts herein, although not expressly illustrated.

The present invention is also pharmaceutical compositions for treating pain, inflammation or migraine comprising an analgesic, antiinflammatory, or antimigraine effective amount of a compound of formula I as defined above or their pharmaceutically acceptable base or acid addition salts and a pharmaceutically acceptable carrier. Such compositions may be one of a broad range of known forms for topical or systemic administration.

The methods of use are for the treatment in mammals, particularly in humans, of various conditions such as enumerated above either for diseases known as inflammatory or for pain and for migraine. An ordinarily skilled physician would recognize such conditions. The compounds of formula I are active in animal tests which are generally recognized as predictive for antiinflammatory, analgesic or antimigraine activity. Regardless of the route of administration selected, the compounds of the present invention are formulated into pharmaceutically acceptable dosage forms by conventional methods known to the pharmaceutical art. In general a preferred method of administration is, however, by oral dosage forms.

The compounds of formula I can be administered in such unit oral dosage forms as tablets, capsules, pills, powders, or granules. They may also be administered rectally or vaginally in such forms as suppositories or bougies. They may also be introduced parenterally, (e.g., subcutaneously, intravenously, or intramuscularly), using forms known to the pharmaceutical art. Finally, the compounds of formula I can be administered topically using forms known to the pharmaceutical art for application through the skin, by nasal application or in the eye.

An effective but nontoxic amount of the compound of formula I or the salts thereof is employed in treatment. The dosage regimen for treating inflammation, pain or, particularly migraine, by the compounds of formula I and their salts as described above is selected in accordance with a variety of factors including the type, age, weight, sex, and medical condition of the subject, the severity of the inflammation, pain and particularly migraine, the route of administration and the particular compound employed. Determination of the proper dosage for a particular situation is within the skill of the art. Generally, treatment is initiated with smaller dosages which are less than the optimum dose of the compound. Thereafter the dosage is increased by small increments until the optimum effect under the circumstances is reached. For convenience, the total daily dosage may be divided and administered in portions during the day if desired.

Initial dosages of the compounds of the invention are ordinarily in the area of 0.1 mg/kg up to at least 100 mg/kg per dose orally, preferably 0.5 to 30 mg/kg orally are given. Each dose is given from one to four times daily or as needed. When other forms of administration are employed equivalent doses are administered.

Generally, the activity for use as described above for the novel compounds of the present invention is shown as an $ED_{50}$ for illustrative compounds of formula I when administered in a test essentially as described by Koster et al. [Fed. Proc., Vol. 18 (1959), p. 412] in which the peritoneal injection of acetic acid to mice provokes repeated stretching and twisting movements which persist for more than 6 hrs. Analgesics prevent or surpress these syndromes which are considered to be an exteriorization of a diffuse abdominal pain. The results are expressed as mg/kg which amount produces the desired inhibition of stretching or "writhing" in 50 percent of a population.

The protocol and the results are particularly as follows:

ANTIWRITHING TEST IN MICE (AW) TEST PROTOCOL

The purpose of this test is to evaluate drugs for analgesic activity.

METHOD

SUBJECTS

Subjects are male Swiss-Webster mice (25–35 g).

DRUGS

A compound of formula I is dissolved or suspended in physiological saline containing 2% Emulphor. Suspensions are subjected to ultrasonication for three minutes. Drug doses are expressed as the active moiety and are normally administered to mice (10, 30, and 100 mg/kg IP, SC, PO, or IM) in a volume of 10 ml/kg, 1 hr prior to testing; ICV doses (in $\mu$g/kg) are administered in a volume of 0.5 ml/kg, 5 min prior to testing. Animals dosed PO are fasted for 16 hours prior to dosing. Groups of eight mice are tested with each dose or the vehicle solution (control group).

PROCEDURE

Mice are treated with a dilute solution of acetic acid (0.6%, 10 ml/kg IP) which elicits writhing. In four successive trials, one pair of mice from each treatment group is placed in one of four adjacent clear plexiglas chambers (4 in×4 in×4 in). This allows the simultaneous observation of four pairs of mice representing all treatments and controls throughout the test. Writhing movements (abdominal contractions, stretching of the torso and hind legs, and concave arching of the back) are counted for five minutes commencing seven minutes after acetic acid administration.

DATA ANALYSIS

Drug effects on acetic acid-induced writhing are expressed as percent suppression of writhing relative to the vehicle-treated control group run in parallel with treated animals. The writhing tallies from pairs of animals are summed for each treatment and are divided by the summed writhing in the control group. The $ED_{50}$s for suppression of writhing are determined by non-linear regression analysis.

TABLE
Antiwrithing Results

| Compound No. | $ED_{50}$ |
|---|---|
| $I^1$ | 11.8 mg/kg ± 0.9292 |
| $I^2$ | 3.4 mg/kg ± 0.8215 |
| $I^3$ | 1.2 mg/kg ± 0.7746 |
| $I^4$ | 22.0 mg/kg ± 0.8220 |
| $I^6$ | 13.0 mg/kg ± 0.8987 |
| $I^7$ | 9.4 mg/kg ± 0.8355 |
| $I^8$ | 1.3 mg/kg ± 0.8184 |
| $I^9$ | 8.0 mg/kg |

DESCRIPTION OF THE PREFERRED EMBODIMENTS

The following Preparations will further illustrate the invention, without limiting it thereto.

Preparations

The preparation of the compound of formula $I^1$ is generally illustrated as follows:

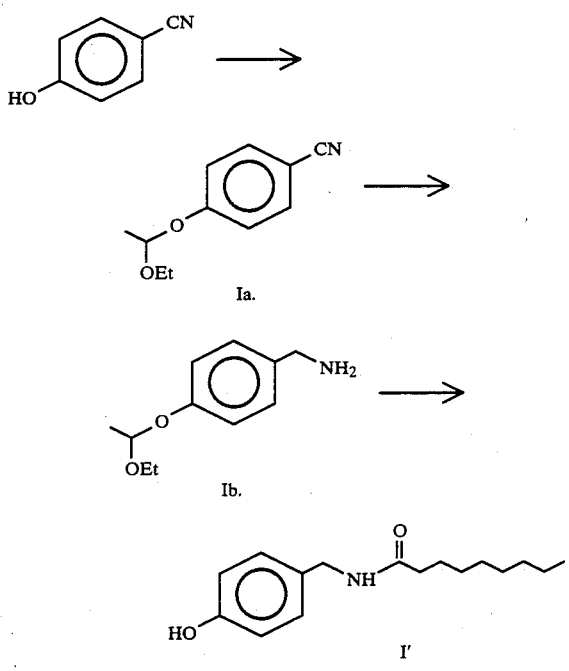

Preparation of Ia

To a mixture of 4-hydroxybenzonitrile (50.00 g, 0.420 mol) and ethyl vinyl ether (82 ml, 0.86 mol) in chloroform (420 ml) is added concentrated hydrochloric acid (0.5 ml). The reaction mixture becomes warm, and a solution forms. The reaction is stirred at ambient temperature for 15 hours, and washed with 1 N NaOH (4×200 ml) and saturated NaCl (200 ml). After drying over MgSO$_4$, the dark oil is purified by distillation (Bp 120° C.; 1.0 mm Hg).

Yield: 58.37 g (72.7%).

Preparation of Ib

A solution of Ia (57.87 g, 0.303 mol) in tetrahydrofuran (125 ml) is added dropwise to a mechanically stirred, ice cooled suspension of lithium aluminum hydride (23.50 g, 0.619 mol) in tetrahydrofuran (615 ml). The resulting greenish mixture is refluxed for 15 hours, cooled in an ice bath and quenched by the dropwise addition of H$_2$O (23.5 ml), 0.5 N NaOH (24 ml), and H$_2$O (24 ml). To the resulting greyish mixture is added 5 N NaOH until the mixture is white, and no grey material remains. The reaction is filtered through celite, and the filtrate evaporated in vacuo. The residue is partitioned between ethyl ether (1000 ml) and H$_2$O (350 ml). The ether layer is washed with saturated NaCl, and dried over K$_2$CO$_3$. Evaporation of the solvent gave the product as a cloudy yellow oil.

Yield: 59.52 g (97.9%). Used as is in next step.

Preparation of I'

Nonamide, N-[(4-hydroxyphenyl)methyl]-

A solution of nonanoyl chloride (20.0 ml, 0.111 mol) in tetrahydrofuran (70 ml) is added dropwise to a stirred solution of Ib (20.02 g, 0.103 mol) and triethylamine (16.0 ml, 0.115 mol) in tetrahydrofuran (175 ml) at +5° C. The reaction is stirred at room temperature for 3 hours and evaporated in vacuo. The residue is taken up in methylene chloride and washed with 1 N HCl, H$_2$O, saturated NaHCO$_3$, H$_2$O, and brine. After drying over MgSO$_4$, the solution is evaporated, and the residue is taken up in tetrahydrofuran (400 ml) and 1 N HCl (135 ml). After stirring for one hour the reaction is evaporated, and the residue taken up in chloroform, washed with 1 N HCl, saturated NaHCO$_3$, and brine. After drying over MgSO$_4$ the solution is evaporated to a yellow solid. Recrystallization from isopropyl ether gives the product o formula I' as a light yellow solid.

Yield: 19.83 g (73.4%), mp 86°-87.5° C.

The preparation of a compound of formula $I^2$ is generally as follows:

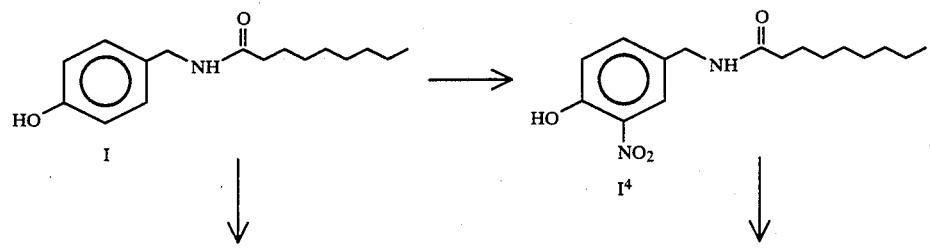

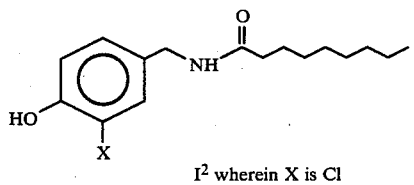

I² wherein X is Cl
I³ wherein X is Br

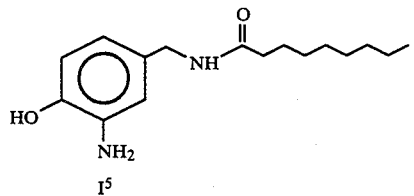

I⁵

Preparation of I²

Nonamide, N-[(3-chloro-4-hydroxyphenyl)methyl]-

A solution of chlorine (2.8 g) in chloroform (90 ml) is added dropwise to a stirred solution of the compound of formula I' (5.00 g, 0.019 mol) in chloroform (300 ml) until all of the compound of formula I' is consumed. The reaction is washed with 1 N HCl, H₂O, and saturated NaCl, and dried over MgSO₄. After evaporation, the resulting oil is chromatographed (Silica gel; 70:25:5 chloroform:hexanes:tetrahydrofuran), and placed under high vacuum for 15 hours. The resulting solid is collected, washed with hexanes, and dried in vacuo.

Yield: 2.90 g (51.3%); mp 64°–66° C.

Preparation of I³

Nonamide, N-[(3-bromo-4-hydroxyphenyl)methyl]-

A solution of bromine (2.55 g, 0.016 mol) in chloroform (100 ml) is added dropwise to an ice cooled, stirred solution of a compound of formula I' (4.00 g, 0.0152 mol) in chloroform (225 ml). The reaction is allowed to stir for 15 hours, is evaporated, and chromatographed (silica gel; 75:20:5 chloroform:hexanes:tetrahydrofuran). Yield: 3.43 g (66.0%); mp 72°–74° C.

Preparation of I⁴

Nonamide, N-[(4-hydroxy-3-nitrophenyl)methyl]-

A solution of concentrated nitric acid (1.02 g, 0.0113 mol) in acetic acid (10 ml) is added dropwise to a stirred, ice cooled solution of a compound of the formula I' (3.00 g, 0.0114 mol) in acetic acid (60 ml). After stirring for 30 minutes the reaction is evaporated and the residue flash chromatographed (silica gel; 3:1 hexanes:ethyl acetate). The product is recrystallized from cyclohexanes. Yield: 2.19 g (62.3%); mp 95.5°–97° C.

Preparation of I⁵

Nonamide, N-[(3-amino-4-hydroxyphenyl)methyl]-

A solution of the compound of formula I⁴ (2.65 g, 8.59 mmol) in methanol/tetrahydrofuran (50/50; 100 ml) is hydrogenated over Raney nickel (0.3 g) at 50 psi. The solution is evaporated and the residue recrystallized from hexanes/ethyl acetate. Yield: 1.58 g (65.5%); mp 141°–143° C.

The preparation of the compounds of the formula I⁶ and of the formula I⁷ is generally illustrated as follows:

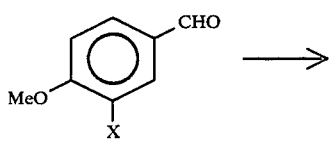

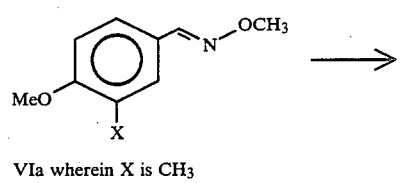

VIa wherein X is CH₃
VIIa wherein X is F

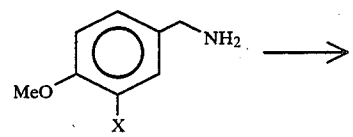

VIb wherein X is CH₃
VIIb wherein X is F

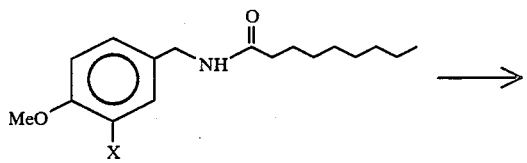

VIc wherein X is CH₃
VIIc wherein X is F

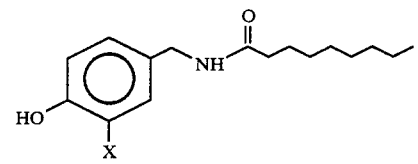

I⁶ wherein X is CH₃
I⁷ wherein X is F

Preparation of VIa

To a stirred solution of 3-methyl-p-anisaldehyde (10.00 g, 0.0666 mol) and methoxyamine hydrochloride (5.90 g, 0.0706 mol) in methanol (333 ml) is added, dropwise, 1 N NaOH (73 ml). After stirring for 5 days at room temperature, the reaction is evaporated, and the residue partitioned between chloroform and water. The water layer is extracted twice more with chloroform, and the chloroform extracts are combined and washed with 1 N HCl, H₂O, saturated NaHCO₃, H₂O, and saturated NaCl. After drying over MgSO₄, the solution is evaporated to a colorless oil. The product of formula VIa obtained as an oil having a yield of 11.48 g (96.2%) is used as is in the next step.

Preparation of VIb

A solution of product of formula VIa (5.91 g, 0.0330 mol) in MeOH/NH₃ (saturated, 100 ml) is hydrogenated over Raney nickel (2.0 g, washed with MeOH) at 50 psi. The solution is evaporated and flash chromatographed (silica gel; 95:5:0.5 chloroform:methanol:ammonium hydroxide) to yield a compound of the formula VIb as a yellow oil. Yield: 4.39 g (86.7%).

Preparation of VIc

A solution of nonanoyl chloride (2.45 g, 0.0139 mol) in tetrahydrofuran (25 ml) is added dropwise to a stirred, ice cooled solution of compound VIb as prepared above (2.00 g, 0.0132 mol) and triethylamine (2.0 ml, 0.0143 mol) in tetrahydrofuran (75 ml). After stirring for 3 hours, the reaction is evaporated, and the residue taken up in methylene chloride (100 ml). The solution is washed with $H_2O$, 1 N HCl, $H_2O$, saturated $NaHCO_3$, $H_2O$, and saturated NaCl. After drying over $MgSO_4$ the evaporated product is flash chromatographed (silica gel; 3:1 hexanes:ethyl acetate) to yield a compound of the formula VIc as a white solid. Yield: 2.71 g (70.3%).

Preparation of $I^6$

Nonamide, N-[(4-hydroxy-3-methylphenyl)methyl]-

A solution of boron tribromide in methylene chloride (1.0 M, 30 ml, 30 mmol) is added dropwise to a stirred solution of the compound of formula VIc as prepared above (2.41 g, 8.26 mmol) in chloroform (50 ml) under nitrogen. After stirring at room temperature for 30 minutes, the solution is refluxed for ten minutes, and then cooled to 5° C. in an ice bath. The reaction is quenched with methanol (20 ml), and evaporated. The residue is taken up in chloroform (100 ml) and washed with $H_2O$, 1 N HCl, $H_2O$, saturated $NaHCO_3$, $H_2O$, and saturated NaCl. After drying over $MgSO_4$ the product is flash chromatographed (silica gel; 2:1 hexanes:ethyl acetate) to yield an oil which solidified on standing. Recrystallized from hexanes/ethyl acetate to give the product of formula $I^6$. Yield: 1.55 g (67.6%); mp 64°–66° C.

Preparation of VIIa

A solution of 3-fluoro-4-methoxybenzaldehyde (15.00 g, 97.3 mmol) in methanol (300 ml) is added to a stirred, ice cooled solution of methoxyamine hydrochloride (8.40 g, 101 mmol) and 1 N NaOH (105 ml, 105 mmol) in methanol (180 ml). After stirring at room temperature for 16 hours, the solution is evaporated, and the residue partitioned between ethyl ether and water. The ether layer is washed with saturated $NaHCO_3$, dried over $K_2CO_3$, and evaporated to yellowish-white crystalline plates. Recrystallization from hexanes gives the compound of formula VIIa. Yield: 15.10 g (84.7%); mp 52°–55° C.

Preparation of VIIb

A solution of the compound of formula VIIa as prepared above (15.00 g, 81.9 mmol) in MeOH/NH₃ (saturated, 150 ml) is hydrogenated over Raney nickel (5 g) at 50 psi. The resulting cloudy solution is evaporated and vacuum distilled to give a product of the formula VIIb (Bp 95° C. at 0.8 mm Hg). Yield: 11.88 g (93.2%).

Preparation of VIIc

A solution of nonanoyl chloride (6.0 ml, 32.6 mmol) in tetrahydrofuran (25 ml) is added to a stirred, ice cooled solution of the compound of formula VIIb as prepared above (5.00 g, 32.2 mmol) and triethylamine (4.6 ml, 33.0 mmol) in tetrahydrofuran (100 ml) under nitrogen. The stirred reaction is warmed to room temperature, evaporated, and the residue partitioned between 1 N HCl and chloroform. The aqueous layer is extracted once with chloroform, and the chloroform extracts combined. After washing the extracts with 1 N HCl, $H_2O$, saturated $NaHCO_3$, $H_2O$, and saturated NaCl, the product having the formula VIIc is evaporated as a white solid. Yield: 8.79 g (92.3%); mp 83°–85° C.

Preparation of $I^7$

Nonamide, N-[(3-fluoro-4-hydroxyphenyl)methyl]-

A solution of boron tribromide in methylene chloride (1.0 M, 49 ml, 49 mmol) is added dropwise to a stirred solution of the compound of formula VIIc as prepared above (4.00 g, 13.5 mmol) in chloroform (80 ml) under a nitrogen atmosphere. After stirring at room temperature for 30 minutes, the solution is refluxed for ten minutes, and then cooled to +5° C. The reaction is quenched with methanol (32 ml), and evaporated. The residue is flash chromatographed (silica gel; 70:25:5 chloroform:hexanes:tetrahydrofuran) to yield a compound of the formula $I^7$ as a white solid. Yield: 3.02 g (79.3%); mp 51°–53° C.

The preparation of the compound of formula $I^8$ is generally illustrated as follows:

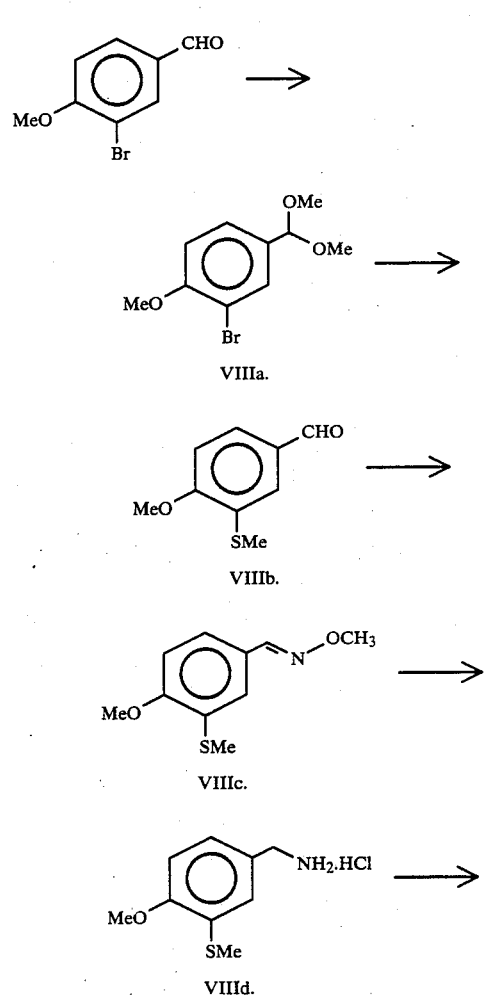

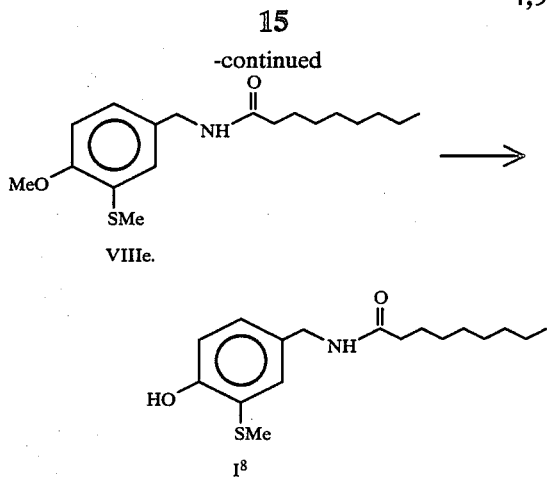

VIIIe.

I⁸

Preparation of VIIIa

A solution of 3-bromo-4-methoxybenzaldehyde (20.00 g, 93.0 mmol) and concentrated hydrochloric acid (1 ml) in methanol (400 ml) is stirred at room temperature for 48 hours. After evaporation of the solvents the residue is partitioned between chloroform and water, and the organic layer washed with saturated NaHCO$_3$, H$_2$O, and saturated NaCl. After drying over K$_2$CO$_3$, the solution is evaporated, and the resulting oil vacuum distilled to give the product of formula VIIIa. Yield: 21.12 g (87.0%); Bp 110° C. (0.8 mm Hg).

Preparation of VIIIb

A solution of the compound of formula VIIIa as prepared above (15.00 g, 57.4 mmol) in anhydrous tetrahydrofuran (150 ml) is added dropwise to a stirred suspension of magnesium turnings (1.41 g, 58.0 mmol) in anhydrous tetrahydrofuran (45 ml) under a nitrogen atmosphere. (Several drops of ethylene dibromide are added to initiate the reaction.) The reaction mixture is refluxed for 2 hours, cooled to room temperature, and a solution of methyl disulfide (5.41 g, 57.4 mmol) in anhydrous tetrahydrofuran (75 ml) is added dropwise. The solution is refluxed for 2 hours, and cooled to 10° C. To the reaction mixture is added 20% NH$_4$Cl (260 ml) while keeping the temperature below 20° C. The resulting biphasic mixture is extracted with ethyl ether (2×150 ml). The ethereal extracts are combined, washed with brine, and dried over MgSO$_4$. After evaporation, the crude product is flash chromatographed (silica gel; 4:1 hexanes:ethyl acetate). The purified product is taken up in tetrahydrofuran and stirred with 3 N HCl (25 ml) for ten minutes. The solution is evaporated, and the residue partitioned between H$_2$O (50 ml) and ethyl ether (50 ml). The water layer is extracted once more with ether (50 ml) and ethereal extracts combined. After washing with saturated NaCl and drying over MgSO$_4$, the solution is evaporated to give a product of the formula VIIIb as a thick, yellow oil. Yield: 4.19 g (40.0%).

Preparation of VIIIc

To an ice cold, stirred solution of methoxyamine hydrochloride (3.03 g, 36.3 mmol) in methanol (65 ml) is added, dropwise, 1 N NaOH (40 ml). To this is then added a solution of a compound of the formula VIIIb as prepared above (6.40 g, 35.1 mmol) in methanol (110 ml). The reaction solution is stirred at room temperature for 15 hours, and then evaporated. The residue is partitioned between chloroform and water. The water layer is extracted once more with chloroform, and the combined chloroform extracts are washed with H$_2$O, 1 N HCl, H$_2$O, saturated NaHCO$_3$, H$_2$O, and saturated NaCl. After drying over MgSO$_4$, the solution is evaporated, and the crude product of formula VIIIc flash chromatographed (silica gel; 5:1 hexanes:ethyl acetate). Yield: 6.12 g (82.8%).

Preparation of VIIId

A solution of trifluoroacetic acid (10.94 ml, 142 mmol) in tetrahydrofuran (15 ml) is added dropwise to a stirred suspension of sodium borohydride (5.37 g, 142 mmol) in tetrahydrofuran (140 ml) under a nitrogen atmosphere while keeping the temperature between 17 and 22° C. To the resulting solution is then added a solution of a compound of the formula VIIIc as prepared above (6.00 g, 28.4 mmol) in tetrahydrofuran (15 ml). The reaction mixture is stirred at ambient temperature for 2 hours, and then refluxed for 2 hours. After cooling to 5° C., the mixture is carefully quenched with water (20 ml) while keeping the temperature below 10° C. The resulting mixture is evaporated to near dryness, and the residue partitioned between 1 N NaOH and methylene chloride. The water layer is extracted twice more with methylene chloride. The organic extracts are combined and washed with 1 N NaOH, H$_2$O, and saturated NaCl. After drying over K$_2$CO$_3$, the filtered solution is acidified with 6 N HCl in isopropyl alcohol. The milky solution is evaporated, and the residue triturated with ethyl ether. The solid product of the formula VIIId is filtered, washed with ether, and dried in vacuo then recrystallized from methanol/ethyl ether. Yield: 4.26 g (68.3%); mp 232°–234° C.

Preparation of VIIIe

A solution of nonanoyl chloride (3.4 ml, 18.5 mmol) in tetrahydrofuran (25 ml) was added dropwise to a stirred, ice cold, solution of a compound of the formula VIIId as prepared above (3.80 g, 17.4 mmol) and triethylamine (5.4 ml, 38.7 mmol) in 1-methyl-2-pyrrolidone (75 ml) under a nitrogen atmosphere while keeping the temperature less than 15° C. The reaction is stirred at room temperature for 63 hours, poured into 500 ml H$_2$O, and extracted with ethyl acetate (5×100 ml). The organic extracts are combined, washed with 1 N HCl, H$_2$O, saturated NaHCO$_3$, H$_2$O, saturated NaCl, and dried over MgSO$_4$. Evaporation yields a product of the formula VIIIe as a white solid. Yield: 3.96 g (70.8%); mp 96°–97° C.

Preparation of I⁸

Nonamide,
N-[(4-hydroxy-3(methylthio)phenyl)methyl]-

A 1.0 M solution of boron tribromide in methylene chloride (39 ml, 39 mmol) is added dropwise to a stirred solution of a compound of the formula VIIIe as prepared above (3.38 g, 10.4 mmol) in chloroform (70 ml) under a nitrogen atmosphere. The mixture is stirred at room temperature for 30 minutes, refluxed for 40 minutes and stirred at room temperature for 15 hours. The ice cooled reaction is quenched with methanol (40 ml). After evaporation, the residue is taken up in chloroform (100 ml) and washed with 1 N HCl, H$_2$O, and saturated NaCl. After drying over MgSO$_4$, the product of the formula I⁸ is evaporated and flash chromatograhed (70:23:7 chloroform:hexanes:tetrahydrofuran). The resulting thick oil crystallized on standing under high vacuum. Yield: 2.60 g (80.4%); mp 69.5°-71.5° C.

In a similar manner using corresponding starting materials the compound of formula I⁹ which is nonanamide, N-[(3-amino-4-hydroxyphenyl)methyl]- was prepared, mp 141°-143° C.

We claim:

1. A compound of the formula

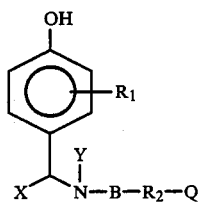

and pharmaceutically acceptable acid addition or base salts thereof; wherein:
(a) $R_1$ is (i) R wherein R is lower alkyl or NR'R" wherein R' and R" are independently hydrogen or lower alkyl, (ii) halogen, (iii) trifluoromethyl, (iv) $NO_2$, (v) $SCH_3$, (vi) $SO_2R'$ wherein R' is as defined above, (viii) NHCOR' wherein R' is as defined above, (ix) CN, or (x) 5-tetrazolyl;
(b) B is

 (B₁)

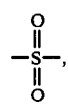 (B₂)

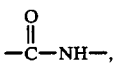 (B₃)

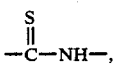 (B₄)

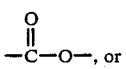 (B₅)

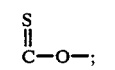 (B₆)

(c) X and Y are independently H or lower alkyl,
(d) $R_2$ is alkylenyl, alkenylenyl, alkynylenyl of 1 to 23 carbons, inclusive; (e) Q is (i) $R_3$ wherein $R_3$ is lower alkyl or NR'R" wherein R' and R" are independently as defined above; (ii) halogen; (iii) trifluoromethyl; (iv) $NO_2$; (v) $SCH_3$; (vi) $SO_2R'$ wherein R' is independently as defined above; (vii) COR' wherein R' is independently as defined above; (viii) NHCOR' wherein R' is independently as defined above; (ix) CN; (x) tetrazolyl; (xi) imidazolyl; (xii) cyclohexyl; (xiii) phenyl; or

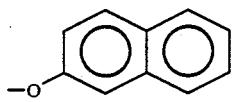 (xiv)

with the proviso that $R_1$ cannot be straight or branched lower alkyl ortho to the OH when X and Y are hydrogen, B is

$R_2$ is alkylenyl or alkenylenyl and Q is lower alkyl; and with the additional proviso that $R_1$ cannot be halogen, $CO_2R'$, $SCH_3$ or NHCOR' when X and Y are hydrogen, B is

$R_2$ is alkylenyl or alkenylenyl of up to 6 carbon atoms and Q is $CH_3$.

2. A compound according to claim 1 having the formula:

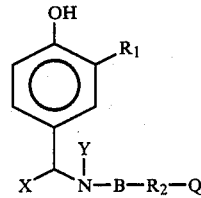

wherein X, Y, B, $R_1$, $R_2$ and Q are as defined above.

3. A compound according to claim 2 wherein B is $B_1$.

4. A compound according to claim 3 wherein $R_2$ is an alkylenyl chain of 3 to 11 carbons, inclusive.

5. A compound according to claim 4, and being N-[(3-chloro-4-hydroxyphenyl)methyl]nonamide.

6. A compound according to claim 4, and being N-[(3-bromo-4-hydroxyphenyl)methyl]nonamide.

7. A compound according to claim 4, and being N-[(4-hydroxy-3-nitrophenyl)methyl]nonamide.

8. A compound according to claim 4, and being N-[(3-amino-4-hydroxyphenyl)methyl]nonamide.

9. A compound according to claim 4, and being N-[(4-hydroxy-3-methylphenyl)methyl]nonamide.

10. A compound according to claim 4, and being N-[(3-fluoro-4-hydroxyphenyl)methyl]nonamide.

11. A compound according to claim 4, and being N-[[4-hydroxy-3-(methylthio)phenyl]methyl]nonamide.

12. A pharmaceutical composition for treating inflammation, pain or migraine comprising an antiinflammatory, analgesic or antimigraine effective amount of a compound of claim 1 and a pharmaceutically acceptable carrier.

13. A method of reducing inflammation in mammals suffering therefrom which comprises administering to such mammal an effective amount of a compound of claim 1.

14. A method for treating pain in mammals suffering therefrom which comprises administering to such mammal an analgesic effective amount of a compound of claim 1.

15. A method for treating headaches in mammals suffering therefrom which comprises administering to such mammal an antiheadache effective amount of a compound of claim 1.

* * * * *

UNITED STATES PATENT AND TRADEMARK OFFICE
CERTIFICATE OF CORRECTION

PATENT NO. : 4,980,366

DATED : December 25, 1990

INVENTOR(S) : Johnson, et al

It is certified that error appears in the above-identified patent and that said Letters Patent is hereby corrected as shown below:

In column 17, line 25 after "above", add --(vii) $CO_2R$ wherein R' is as defined above,--.

Signed and Sealed this

Tenth Day of August, 1993

Attest:

MICHAEL K. KIRK

*Attesting Officer*  Acting Commissioner of Patents and Trademarks